United States Patent
Curtis

(10) Patent No.: US 9,480,825 B2
(45) Date of Patent: Nov. 1, 2016

(54) CATHETER SYSTEM FOR VENOUS INFUSIONS

(71) Applicant: Guy P. Curtis, San Diego, CA (US)

(72) Inventor: Guy P. Curtis, San Diego, CA (US)

(73) Assignee: THE GUY P. CURTIS AND FRANCES L. CURTIS TRUST, CA (US)

( * ) Notice: Subject to any disclaimer, the term of this patent is extended or adjusted under 35 U.S.C. 154(b) by 0 days.

(21) Appl. No.: 14/275,583

(22) Filed: May 12, 2014

(65) Prior Publication Data

US 2015/0320981 A1 Nov. 12, 2015

(51) Int. Cl.
*A61M 25/10* (2013.01)
*A61M 5/168* (2006.01)

(52) U.S. Cl.
CPC ...... *A61M 25/1002* (2013.01); *A61M 25/1011* (2013.01); *A61M 5/16813* (2013.01); *A61M 25/104* (2013.01); *A61M 2025/105* (2013.01); *A61M 2025/1013* (2013.01); *A61M 2025/1052* (2013.01)

(58) Field of Classification Search
CPC .................... A61M 25/1002; A61M 25/1011; A61M 2025/1004; A61M 2025/1013; A61M 2025/1015
See application file for complete search history.

(56) References Cited

U.S. PATENT DOCUMENTS

| | | | |
|---|---|---|---|
| 4,944,726 A | 7/1990 | Hilal et al. | |
| 5,397,307 A | 3/1995 | Goodin | |
| 5,681,281 A | 10/1997 | Vigil et al. | |
| 5,713,863 A | 2/1998 | Vigil et al. | |
| 5,746,716 A | 5/1998 | Vigil et al. | |
| 5,873,852 A | 2/1999 | Vigil et al. | |
| 6,221,042 B1 | 4/2001 | Adams | |
| 2001/0041880 A1 | 11/2001 | Brisken et al. | |
| 2002/0007180 A1 | 1/2002 | Wittenberger et al. | |
| 2008/0300571 A1* | 12/2008 | LePivert | 604/503 |
| 2009/0275894 A1 | 11/2009 | Curtis | |
| 2011/0270176 A1* | 11/2011 | Ehrenreich | A61M 25/1018 604/99.04 |
| 2011/0313400 A1* | 12/2011 | Boatman | 604/509 |
| 2012/0101476 A1 | 4/2012 | Curtis | |
| 2012/0157913 A1* | 6/2012 | Aziz | A61M 5/14236 604/28 |
| 2012/0165785 A1 | 6/2012 | Schatz | |
| 2014/0081207 A1 | 3/2014 | Schatz | |

OTHER PUBLICATIONS

PCT International Search Report, Application No. PCT/US2015/022656, Mar. 26, 2015.

* cited by examiner

*Primary Examiner* — Imani Hayman
*Assistant Examiner* — James D Ponton
(74) *Attorney, Agent, or Firm* — Nydegger & Associates

(57) ABSTRACT

A system for anchoring a distal end of a catheter at a treatment site includes an elongated catheter shaft that is formed with a lumen and two cone shaped balloon membranes. For the system, the proximal and distal ends of the balloon membranes are affixed to an outer surface of the shaft to establish balloons having inflation chambers between the membranes and the shaft. A first membrane portion of a first balloon membrane extends from the distal end of the membrane end to a balloon membrane midsection and a second membrane portion extends from the midsection to the proximal membrane end. To establish the proper shape for the inflated balloon, the second membrane portion is configured to establish a cone angle, $\alpha$, (relative to a proximally directed portion of the longitudinal axis) that is less than or equal to ninety degrees ($\alpha \leq 90$ degrees).

6 Claims, 4 Drawing Sheets

CATHETER SYSTEM FOR VENOUS INFUSIONS

FIELD OF THE INVENTION

The present invention pertains generally to catheters having an inflatable balloon that can be used to anchor the distal end of the catheter at a target site in the vasculature of a patient. More particularly, the present invention pertains to a balloon system for an infusion catheter that anchors the distal end of the catheter during an infusion procedure. The present invention is particularly, but not exclusively, useful as a balloon system for anchoring the distal end of a catheter in the coronary veins or the coronary sinus.

BACKGROUND OF THE INVENTION

It is often desirable to anchor and properly stabilize the distal end of a catheter at a treatment site of a patient. For example, the accuracy of many procedures relies on establishing and maintaining the position of the distal catheter end at a selected position relative to targeted tissue that is to be treated. For example, consider an infusion procedure. In this context, it is often desirable, and in some cases imperative, to contact targeted tissue with an infusible medicament. For an infusion procedure, failure to properly anchor and maintain the infusion release port(s) at a suitable position relative to the targeted tissue can often result in an ineffective treatment.

Some treatment sites can present obstacles to the proper anchoring of a catheter. These difficulties can arise due to the geometrical/anatomical properties of the treatment site, as well as the features of the surrounding environment. One such treatment site that can present obstacles to anchoring is the coronary sinus. In this regard, the coronary sinus is located on, and moves with, the pulsating heart organ. These pulsations, which occur during a normal sinus rhythm of the heart as it beats, can act to dislodge an anchored catheter.

Another type of treatment site that can cause difficulties when attempting to properly anchor a catheter includes small vessel treatment sites, such as the veins which empty into the coronary sinus. These small vessels often generate push-back forces during a procedure that can act to dislodge an anchored catheter. This is particularly troublesome when the small vessels are located on a pulsating organ such as the heart.

In light of the above, it is an object of the present invention to provide a catheter system having one or more balloons shaped to anchor and stabilize the distal end of a catheter at a treatment site in the coronary sinus. Another object of the present invention is to provide a catheter system having one or more balloons specifically shaped to anchor and stabilize the distal end of a catheter in a relatively small vein, without being subject to push-back during a treatment operation. Yet another object of the present invention is to provide a catheter system for venous infusions that is easy to use, simple to implement and is comparatively cost effective.

SUMMARY OF THE INVENTION

In accordance with the present invention, a system for anchoring a distal end of a catheter at a treatment site includes an elongated catheter shaft that is formed with a lumen. Once the distal catheter end has been anchored, the system can be used to perform a procedure, such as an infusion procedure, in which a medicament is introduced into a coronary sinus or into one of the veins which drain into the coronary sinus.

For the system, the catheter shaft defines a longitudinal axis and extends from a proximal end to a distal end. In addition to the shaft, the system includes a cone shaped balloon membrane. To establish a balloon, the proximal and distal ends of the balloon membrane are affixed to an outer surface of the shaft. With this arrangement, an inflation chamber is established between the balloon membrane and the outer surface of the shaft. In more structural detail, the balloon membrane includes a first portion that extends from the distal end of the balloon membrane to a balloon membrane midsection. For example, the midsection of the balloon membrane may be shaped as a circular edge. In addition, the balloon membrane includes a second portion that extends from the midsection to the proximal end of the balloon membrane.

To establish the proper shape for the inflated balloon, the second membrane portion is configured to establish a cone angle, $\pm\alpha$, relative to the longitudinal axis, that is less than or equal to ninety degrees ($\alpha \leq 90$ degrees). Typically, for the present invention, the cone angle, $\alpha$, is in a range between about 80 degrees and about 90 degrees. Also, the first portion of the membrane is configured to establish a cone angle, $\beta$, relative to a proximally directed portion of the longitudinal axis, that is less than the cone angle, $\alpha$, and is typically in a range between about 30 degrees and about 60 degrees ($30° < \beta < 60°$) and it can have either a proximal or a distal inclination.

In addition to the shaft and the balloon described above, the system can include an inflation unit that is connected in fluid communication with the inflation chamber of the balloon and used to inflate the balloon. When the system is configured as an infusion catheter, at least one infusion port is provided at the distal catheter end. An infusion unit is then connected in fluid communication with the infusion port for releasing a medicament from the infusion port. In some cases, it may be desirable to allow blood to continue to flow at the treatment site while the balloon is inflated. For this purpose, the shaft can be formed with a hole at a location proximal to the balloon membrane and an opening at a location distal to the balloon membrane. When used, the hole and opening are connected to a common shaft lumen to allow blood to flow between the hole and the opening.

With the above in mind, two embodiments are contemplated for the present invention: a single balloon embodiment (with a balloon as described above) and a double balloon embodiment. As detailed further herein, the single balloon embodiment is particularly suitable for anchoring the distal catheter end in a coronary vein while the double balloon embodiment is particularly suitable for anchoring the distal catheter end in a coronary sinus.

For the double balloon embodiment, the balloon described above is augmented with a second balloon. In more detail, the second balloon is positioned on the shaft at a location distal to the first balloon. With this arrangement, a plurality of perfusion ports can be formed on the shaft between the first balloon and the second balloon. Like the first balloon, the second balloon can include a cone shaped balloon membrane having a proximal end affixed to an outer surface of the shaft and a distal end affixed to the outer surface of the shaft. Structurally, this combination establishes an inflation chamber for the second balloon between the balloon membrane and the outer surface of the shaft.

For the double balloon embodiment, the balloon membrane of the second balloon has a first portion that extends from the proximal end of the balloon membrane to a balloon membrane midsection. Also for the second balloon, the membrane includes a second portion that extends from the midsection to the distal end of the balloon membrane. To establish the proper shape for the second balloon when inflated, the first membrane portion is configured to establish a cone angle, $\beta_2$, with a distally directed portion of the longitudinal axis of the shaft. Typically, the cone angle, $\beta_2$, is in a range between about 30 degrees and about 60 degrees ($30°<\beta<60°$). In addition, the second membrane portion of the second balloon establishes a cone angle, $\alpha_2$, with the longitudinal axis of the shaft, with $\alpha_2 \leq 90$ degrees. Typically, the cone angle, $\alpha_2$, is in a range between about 80 degrees and about 90 degrees and it can have either a proximal or distal inclination.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
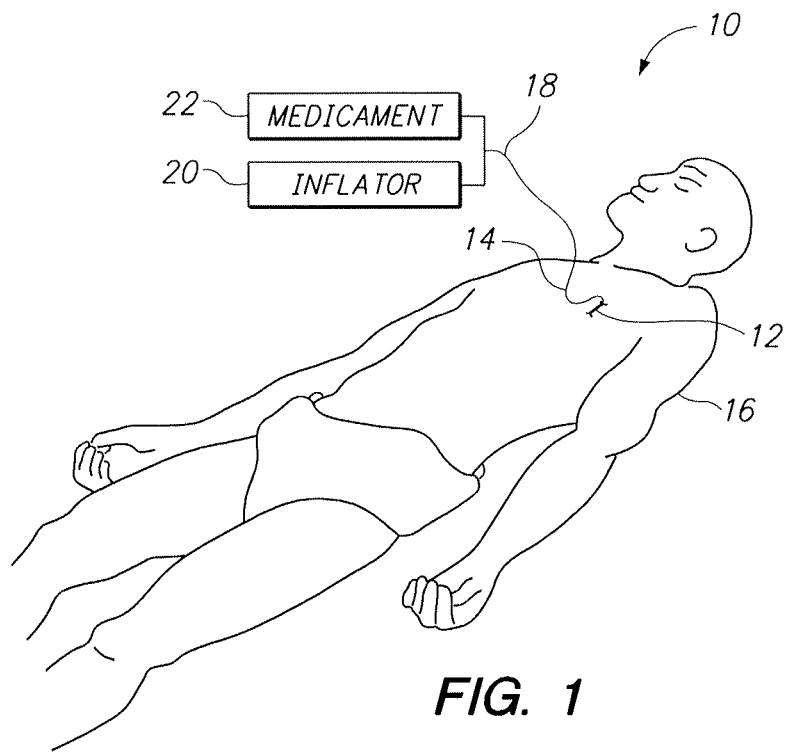
FIG. 1 shows the present invention being used in its intended operational environment.

Referring initially to FIG. 1 a system in accordance with the present invention is shown and is generally designated 10. As shown, the system 10 can be used to position and anchor a distal end 12 of a catheter shaft 14 at a treatment site within the vasculature of a patient 16. FIG. 1 further shows that the proximal end 18 of the catheter shaft 14 can be operationally coupled with an inflation unit 20 and an infusion unit 22. With the shown arrangement, the system 10 can be used to perform a procedure such as an infusion procedure. For example, a fluid, such as an anti-arrhythmic medicament and/or a dye, can be introduced into a coronary sinus or into the veins which drain into the coronary sinus.

Figure 2:
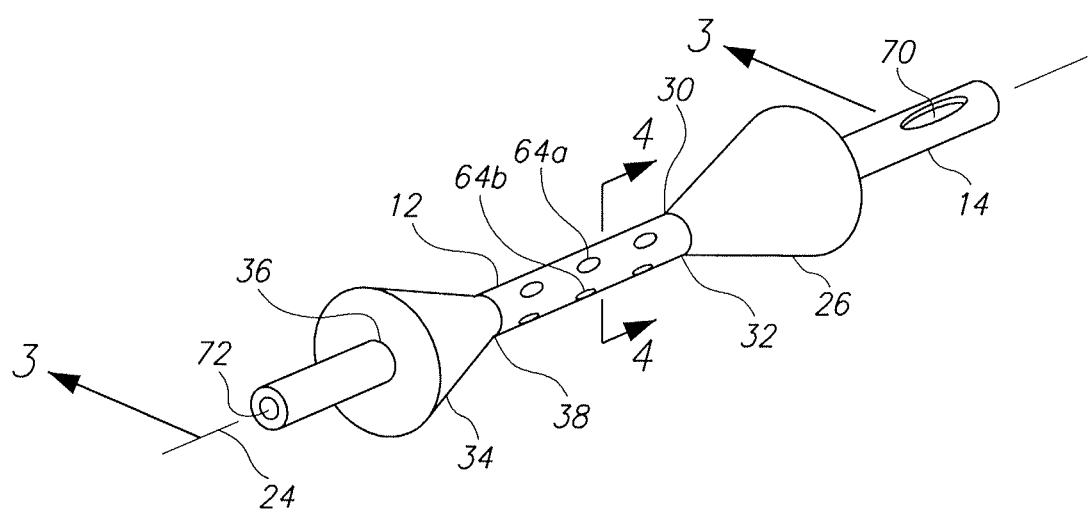
FIG. 2 is a perspective view of the distal section of a venous catheter in accordance with the present invention with its anchoring balloons inflated.

FIG. 2 shows the distal end 12 of the catheter shaft 14 in more detail. As seen there, the catheter shaft 14 is elongated and defines a longitudinal axis 24 in the direction of shaft elongation. It can further be seen that a first cone shaped balloon membrane 26 is mounted on the shaft 14. Specifically, the proximal end 28 (see FIG. 3) and the distal end 30 of the balloon membrane 26 are affixed to an outer surface 32 of the shaft 14 to establish a first balloon. For the embodiment shown in FIG. 2, a second cone shaped balloon membrane 34 is mounted on the shaft 14. Specifically, the distal end 36 and proximal end 38 of the balloon membrane 34 are affixed to the outer surface 32 of the shaft 14 to establish a second balloon.

Figure 3:
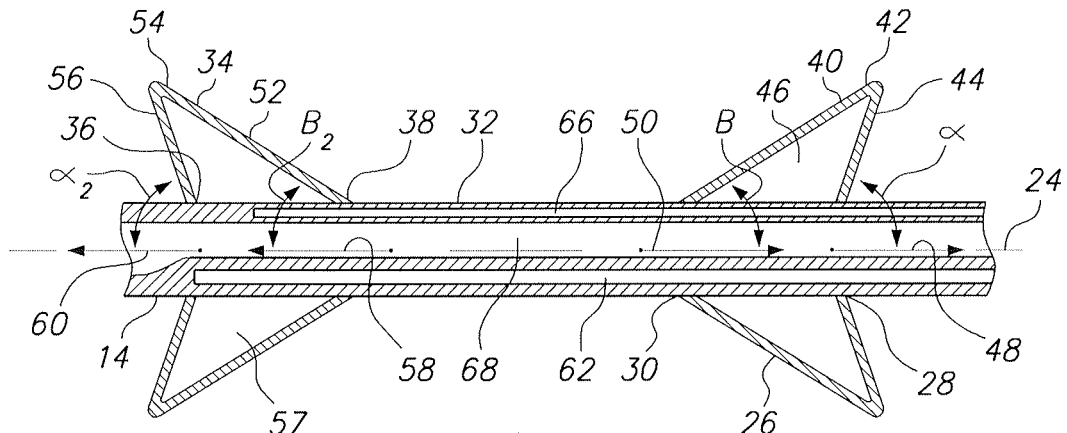
FIG. 3 is a cross-section view of the venous catheter as seen along the line 3-3 in FIG. 2.

The structural details of the balloon membranes 26, 34 can be appreciated with cross-reference to FIGS. 2 and 3. In more structural detail, the balloon membrane 26 includes a first portion 40 that extends from the distal end 30 of the balloon membrane 26 to a balloon membrane midsection 42. For example, the midsection 42 may be shaped as a slightly rounded, circular edge, as shown. Other midsection shapes are possible. Also shown, the balloon membrane 26 includes a second portion 44 that extends from the midsection 42 to the proximal end 28 of the balloon membrane 26. With this arrangement, an inflation chamber 46 is established between the balloon membrane 26 and the outer surface 32 of the shaft 14.

FIG. 3 further shows that after inflation of the balloon membrane 26, the second membrane portion 44 is configured to establish a cone angle, $\alpha$, (relative to a proximally directed portion [arrow 48] of the longitudinal axis 24) that is less than or equal to ninety degrees ($\alpha \leq 90$ degrees). Typically, for the present invention, the cone angle, $\alpha$, is in a range between about 80 degrees and about 90 degrees. Also shown, the first portion 40 of the membrane 26 is configured to establish a cone angle, $\beta$, (relative to a proximally directed portion [arrow 50] of the longitudinal axis 24) that is in a range between about 30 degrees and about 60 degrees.

FIG. 3 also shows that the balloon membrane 34 has a first portion 52 that extends from the proximal end 38 of the balloon membrane 34 to a balloon membrane midsection 54. Also, the balloon membrane 34 includes a second portion 56 that extends from the midsection 54 to the distal end 36 of the balloon membrane 34. With this arrangement, an inflation chamber 57 is established between the balloon membrane 34 and the outer surface 32 of the shaft 14.

As shown in FIG. 3, after inflation of the balloon membrane 34, the first membrane portion 52 is configured to establish a cone angle, $\beta_2$, with a distally directed portion (arrow 58) of the longitudinal axis 24 of the shaft 14. Typically, the cone angle, $\beta_2$, is in a range between about 30 degrees and about 60 degrees. In addition, the second membrane portion 56 of the second balloon establishes a cone angle, $\alpha_2$, with a distally directed portion (arrow 60) of the longitudinal axis 24 of the shaft 14, with $\alpha_2 \leq 90$ degrees. Typically, the cone angle, $\alpha_2$, is in a range between about 80 degrees and about 90 degrees.

Figure 4:
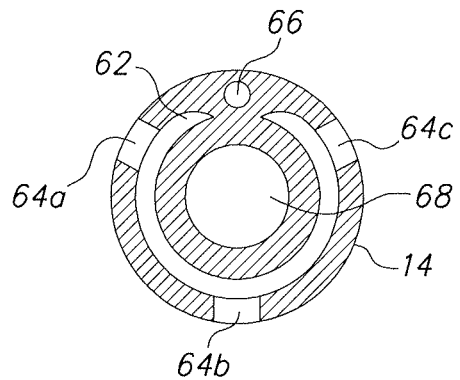
FIG. 4 is a cross-section view of the venous catheter as seen along the line 4-4 in FIG. 2.

FIGS. 3 and 4 also show the details of a representative shaft 14 for use in the present invention. As shown there, the shaft 14 can be formed with a medicament channel 62 that is in fluid communication with a plurality of perfusion ports 64 (see also FIG. 2). The medicament channel 62 is also in fluid communication with the infusion unit 22 (see FIG. 1) allowing a medicament to be pumped through the shaft 14 and released through one of the perfusion ports 64a-c.

FIGS. 3 and 4 also show that the shaft 14 can be formed with an inflation channel 66 that is in fluid communication with the inflation chambers 46, 57 established by the balloon membranes 26, 34, respectively. The inflation channel 66 is also in fluid communication with the inflation unit 20 (see FIG. 1) allowing an inflation fluid to be selectively pumped through the shaft 14 and into one or both of the inflation chambers 46, 57.

FIGS. 3 and 4 also show that the shaft 14 can be formed with a blood flow lumen 68 that establishes fluid communication between a hole 70 (see FIG. 2) at a location proximal to the balloon membrane 26 and an opening 72 at a location distal to the balloon membrane 26. With this arrangement, blood can continue to flow at the treatment site while the balloon(s) is (are) inflated.

Figure 5:
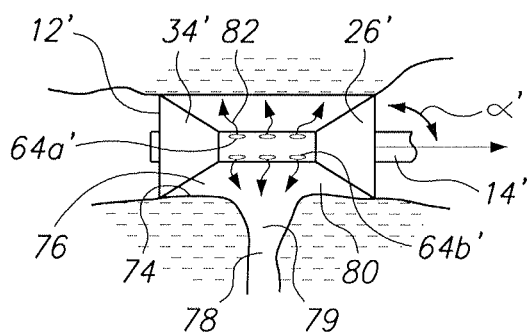
FIG. 5 is an elevation view of the venous catheter of the present invention with the catheter operationally positioned in a coronary sinus of a patient.

FIG. 5 illustrates an operation of the present invention for a double-balloon embodiment having a cone angle, α', of 90 degrees (α'=90). For the operation, the distal end 12' of elongated catheter shaft 14' is advanced to a treatment site 74 in the vasculature. There, at the treatment site 74, balloons having balloon membranes 26', 34' are inflated to contact the inner wall of the vasculature at the treatment site 74 and anchor the distal end 12' of the catheter shaft 14'. Specifically, FIG. 5 shows the distal end 12' positioned in the coronary sinus 76 and across a vein 78 which feeds into the coronary sinus 76 at an ostium 79. As shown, the distal end 12' can be positioned with balloon membrane 34' on one side of the ostium 79 of the vein 78 and balloon membrane 26' on the other side of the ostium 79 of the vein 78. With this arrangement, a reservoir 80 is established between the balloon membranes 26', 34'. Once anchored, an infusion unit 22 (see FIG. 1) is activated to release a medicament (arrow 82) from a plurality of perfusion ports 64a', 64b'.

Figure 6:
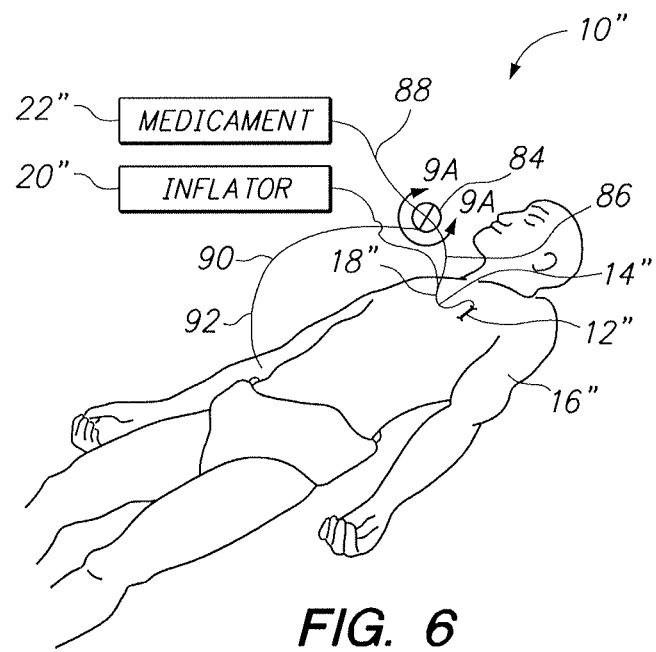
FIG. 6 shows another embodiment of the present invention being used in its intended operational environment.

FIG. 6 shows another embodiment of a system in accordance with the present invention that is generally designated 10". As shown, the system 10" can be used to position and anchor a distal end 12" of a catheter shaft 14" at a treatment site within the vasculature of a patient 16". FIG. 6 further shows that the proximal end 18" of the catheter shaft 14" can be operationally coupled with an inflation unit 20" and an infusion unit 22". With the arrangement shown, the system 10" can be used to perform a procedure such as an infusion procedure. For example, a fluid, such as an anti-arrhythmic medicament, can be introduced into a coronary sinus 76 or into the veins 78 which drain into the coronary sinus 76 (See FIG. 5).

Figure 7:
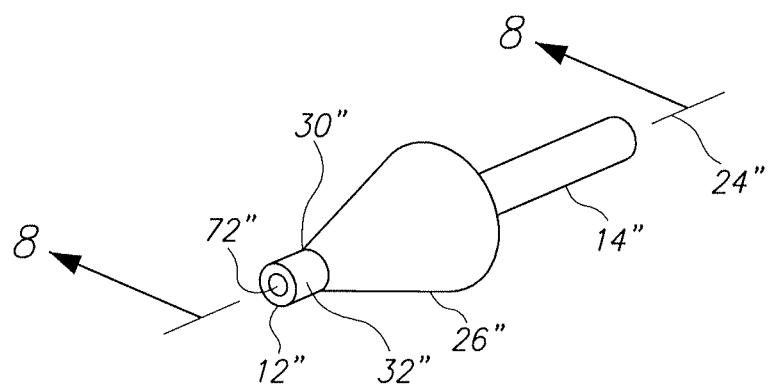
FIG. 7 is a perspective view of the distal section of the venous catheter for the embodiment shown in FIG. 6 with its anchoring balloon inflated.

FIG. 7 shows the distal end 12" of the catheter shaft 14" in more detail. As seen there, the catheter shaft 14" is elongated and defines a longitudinal axis 24" in the direction of shaft elongation. It can further be seen that a cone shaped balloon membrane 26" is mounted on the shaft 14". Specifically, the proximal end 28" (see FIG. 8) and distal end 30" of the balloon membrane 26" are affixed to an outer surface 32" of the shaft 14" to establish the single balloon.

Figure 8:
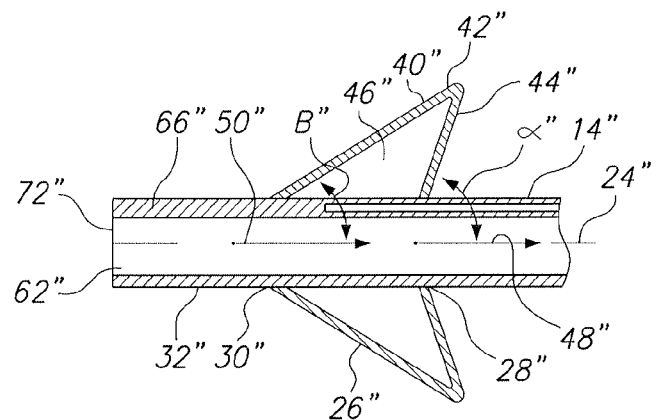
FIG. 8 is a cross-section view of the venous catheter embodiment shown in FIG. 6 as seen along the line 8-8 in FIG. 7.

The structural details of the balloon membrane 26" can be appreciated with cross-reference to FIGS. 7 and 8. In more structural detail, the balloon membrane 26" includes a first portion 40" that extends from the distal end 30" of the balloon membrane 26" to a balloon membrane midsection 42". For example, the midsection 42" may be shaped as a slightly rounded, circular edge, as shown. Other midsection shapes are possible. Also shown, the balloon membrane 26" includes a second portion 44" that extends from the midsection 42" to the proximal end 28" of the balloon membrane 26". With this arrangement, an inflation chamber 46" is established between the balloon membrane 26" and the outer surface 32" of the shaft 14".

FIG. 8 further shows that after inflation of the balloon membrane 26", the second membrane portion 44" is configured to establish a cone angle, α", (relative to a proximally directed portion [arrow 48"] of the longitudinal axis 24") that is less than or equal to ninety degrees (α≤90 degrees). Typically, for the present invention, the cone angle, α, is in a range between about 80 degrees and about 90 degrees. Also shown, the first portion 40" of the membrane 26" is configured to establish a cone angle, β", (relative to a proximally directed portion [arrow 50"] of the longitudinal axis 24") that is in a range between about 30 degrees and about 60 degrees.

An operation of the system 10" can best be appreciated with initial reference to FIG. 6. As shown there, the end 18" of shaft 14" is connected to an extracorporeal valve 84 via line 86. Also, the valve 84 is in fluid communication with the infusion unit 22" via line 88. With this arrangement, the valve 84 (FIG. 6) is placed in fluid communication with the medicament channel 62" (FIG. 8) that terminates in opening 72", establishing a perfusion port for the selective release of medicament into the patient 16". FIG. 6 also shows that a return line 90 is operably coupled to the valve 84 on one end and includes a return line end 92 that can be placed in fluid communication with a peripheral vein or artery of the patient.

Figure 9A:
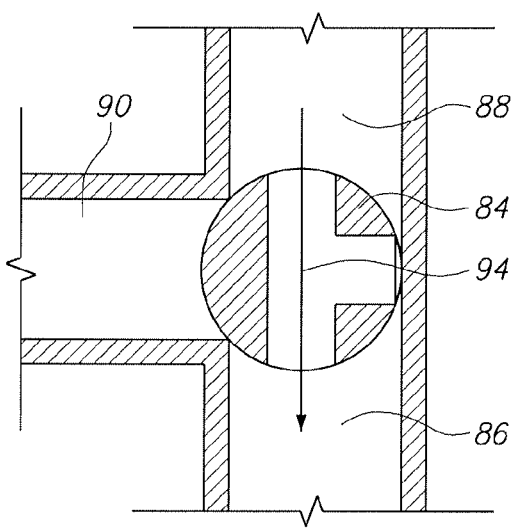
FIG. 9A is an enlarged cross-section, detail view as outlined by arrow 9A-9A in FIG. 6 of a valve, shown configured to introduce a medicament into a patient.
Figure 9B:
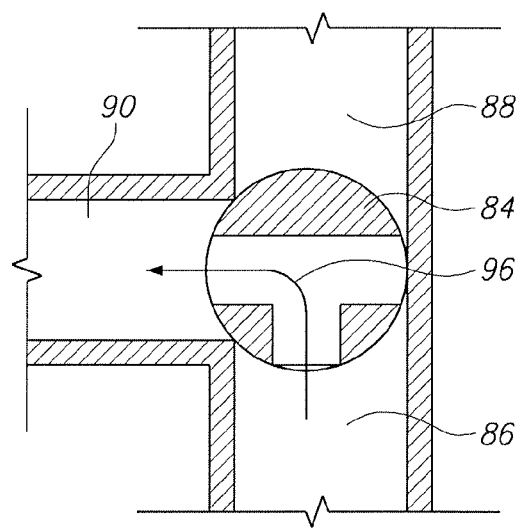
FIG. 9B is an enlarged cross-section, detail view as in FIG. 9A, showing the valve configured to circulate blood through the patient and a return line.

For the operation of the system 10", the distal end 12" (FIG. 6) of elongated catheter shaft 14" is advanced to a treatment site in the vasculature. There, at the treatment site, the balloon membrane 26" is inflated via the inflation channel 66" (FIG. 8) to anchor the distal end 12" (FIG. 6) at the treatment site 74. Once the balloon membrane 26" is anchored, valve 84 is placed into the configuration shown in FIG. 9A wherein the infusion unit 22" (FIG. 6) is in fluid communication with the infusion channel 62" (FIG. 8) and opening 72". With this arrangement, the infusion unit 22" (see FIG. 6) can be activated to pass a medicament through the valve 84 (arrow 94 in FIG. 9A) and into the infusion channel 62" (FIG. 8). With the balloon membrane 26" (FIG. 8) inflated, the valve 84 (FIG. 6) can be reconfigured from the configuration shown in FIG. 9A to the configuration shown in FIG. 9B. In this configuration, the return line 90 is in fluid communication with the infusion channel 62" (FIG. 8) and opening 72". In this configuration, blood is able to flow through a circuit including the return line 90 (FIG. 6), the infusion channel 62" (FIG. 8) and the patient's vasculature. For example, when the return line 90 (FIG. 6) is connected to a peripheral vein, blood is able to flow into the opening 72" (FIG. 8), through the infusion channel 62", through the valve 84 in the direction of arrow 96 in FIG. 9B and into the peripheral vein via return line 90. After allowing blood to circulate for a predetermined period, the valve 84 can be reconfigured into the configuration shown in FIG. 9a, if desired, to perform additional infusion.

While the particular catheter system for venous infusions and corresponding methods of use as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A system for creating a perfusion reservoir in the coronary sinus of a patient, wherein the reservoir is in fluid communication with a vein draining into the coronary sinus, the system comprising:

an elongated shaft formed with a lumen, wherein the shaft defines a longitudinal axis and has a proximal end and a distal end;

a first cone shaped balloon membrane having a proximal end affixed to an outer surface of the shaft and a distal end affixed to the outer surface of the shaft to establish a first cone shaped balloon with an inflation chamber between the first balloon membrane and the outer surface of the shaft, wherein the first balloon membrane has a first portion extending from the distal end of the balloon membrane to a balloon membrane midsection and a second portion extending from the midsection to the proximal end of the first balloon membrane, and wherein the second portion establishes a cone angle, $\alpha$, with a first proximally directed portion of the longitudinal axis of the shaft beginning along the longitudinal axis where the proximal end of the first cone shaped balloon membrane is affixed to the outer surface of the shaft, with $\alpha \leq 90$ degrees;

a second cone shaped balloon membrane having a proximal end affixed to an outer surface of the shaft and a distal end affixed to the outer surface of the shaft to establish a second cone shaped balloon with an inflation chamber between the second balloon membrane and the outer surface of the shaft;

a plurality of perfusion ports formed into the shaft between the distal end of the first cone shaped balloon membrane and the proximal end of the second cone shaped balloon membrane;

an inflation unit connected in fluid communication with the inflation chambers of the first balloon and the second balloon to inflate and respectively anchor the first and second cone shaped balloons to create a reservoir between the inflated balloons, anchored in the coronary sinus over a vein draining into the coronary sinus; and an infusion unit connected in fluid communication with the plurality of perfusion ports to transfer a liquid from the perfusion ports and into the reservoir, for subsequent perfusion of the liquid from the reservoir into the vein.

2. A system as recited in claim 1 wherein the first cone shaped balloon is proximal to the second cone shaped balloon, and wherein the first portion of the first balloon membrane establishes a cone angle, $\beta$, with a second proximally directed portion of the longitudinal axis of the shaft, with $\beta$ in a range between 30 degrees and 60 degrees, and wherein the second balloon membrane has a first portion extending from the proximal end of the second balloon membrane to a balloon membrane midsection and a second portion extending from the midsection to the distal end of the second balloon membrane, and wherein the first membrane portion of the second balloon membrane establishes a cone angle, $\beta_2$, with a first distally directed portion of the longitudinal axis of the shaft, with $\beta_2$ in a range between 30 degrees and 60 degrees and the second membrane portion of the second balloon membrane establishes a cone angle, $\alpha_2$, with a second distally directed portion of the longitudinal axis of the shaft, with $\alpha_2 \leq 90$ degrees.

3. A system for creating a perfusion reservoir in the coronary sinus of a patient, wherein the reservoir is in fluid communication with a vein draining into the coronary sinus, the system comprising:

an elongated shaft formed with a lumen;

a first balloon membrane affixed to an outer surface of the shaft to establish a first cone shaped balloon with an inflation chamber between the first balloon membrane and the outer surface of the shaft wherein the first balloon membrane has a distal end and a proximal end with a first portion thereof extending proximally from the distal end of the first balloon membrane to a first balloon membrane midsection and a second portion thereof extending from the first balloon membrane midsection to the proximal end of the first balloon membrane, and wherein the second portion of the first balloon membrane establishes a cone angle, $\alpha$, with a first proximally directed portion of the longitudinal axis of the shaft beginning along the longitudinal axis where the proximal end of the first cone shaped balloon membrane is affixed to the outer surface of the shaft, with $\alpha \approx 90$ degrees and wherein the first portion of the first balloon membrane establishes a cone angle, $\beta$, with a second proximally directed portion of the longitudinal axis of the shaft, with $\beta$ in a range between 30 degrees and 60 degrees;

a second balloon membrane affixed to the outer surface of the shaft to establish a second cone shaped balloon with an inflation chamber between the second balloon membrane and the outer surface of the shaft wherein the second balloon membrane has a distal end and a proximal end with a first portion thereof extending from the proximal end of the second balloon membrane to a second balloon membrane midsection and a second portion thereof extending from the second balloon membrane midsection to the distal end of the second balloon membrane, and wherein the first membrane portion of the second balloon membrane establishes a cone angle, $\beta_2$, with a first distally directed portion of the longitudinal axis of the shaft, with $\beta_2$ in a range between 30 degrees and 60 degrees and the second membrane portion of the second balloon establishes a cone angle, $\alpha_2$, with a second distally directed portion of the longitudinal axis of the shaft, with $\alpha_2 \leq 90$ degrees;

a plurality of perfusion ports formed into the shaft between the first balloon and the second balloon;

an inflation unit for introducing a fluid into the inflation chamber of the first balloon and into the inflation chamber of the second balloon to inflate the first and second balloons to create a reservoir between the inflated balloons, anchored in the coronary sinus over a vein draining into the coronary sinus; and an infusion unit connected in fluid communication with the plurality of perfusion ports for releasing a medicament into the reservoir created between the first balloon and the second balloon for subsequent perfusion of the liquid from the reservoir into the vein.

4. A system as recited in claim 3 wherein the first balloon is spaced apart from the second balloon along the shaft with the infusion unit connected in fluid communication with the perfusion ports for releasing a medicament from the perfusion ports.

5. A system as recited in claim 3 wherein the second balloon is positioned on the shaft at a location distal to the first balloon and wherein the shaft is formed with a hole at a location proximal to the first balloon and the shaft is formed with an opening at a location distal to the second balloon to allow blood flow between the hole and the opening.

6. A system as recited in claim 3 wherein the first and second balloon membranes are cone-shaped.

* * * * *